(12) United States Patent
Kober et al.

(10) Patent No.: US 6,683,030 B2
(45) Date of Patent: Jan. 27, 2004

(54) AGROTECHNICAL FORMULATION

(75) Inventors: Reiner Kober, Fussgönheim (DE); Matthias Bratz, Limburgerhof (DE); Rainer Berghaus, Speyer (DE); Boris Breitscheidel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/221,201

(22) PCT Filed: Mar. 12, 2001

(86) PCT No.: PCT/EP01/02764
§ 371 (c)(1), (2), (4) Date: Sep. 10, 2002

(87) PCT Pub. No.: WO01/67860
PCT Pub. Date: Sep. 20, 2001

(65) Prior Publication Data
US 2003/0069135 A1 Apr. 10, 2003

(30) Foreign Application Priority Data
Mar. 13, 2000 (DE) .......................... 100 12 161

(51) Int. Cl.⁷ .................. A01N 25/02; A01N 25/04; A01N 43/84

(52) U.S. Cl. .................. 504/313; 504/358; 514/529; 514/785

(58) Field of Search .................. 504/313, 358; 514/529, 785

(56) References Cited

U.S. PATENT DOCUMENTS

| | | | |
|---|---|---|---|
| 4,626,274 A | 12/1986 | Hausmann et al. | 71/93 |
| 4,834,908 A | 5/1989 | Hazen et al. | 252/356 |
| 5,672,564 A | 9/1997 | Wigger et al. | 504/116 |
| 6,087,305 A | 7/2000 | Kober et al. | 504/313 |
| 6,284,917 B1 | 9/2001 | Brunner et al. | 560/127 |

FOREIGN PATENT DOCUMENTS

| | | | |
|---|---|---|---|
| DE | 197 01 123 | * | 8/1997 |
| EP | 0 579 052 | * | 7/1993 |
| SU | 537660 | | 5/1977 |
| WO | WO 92/06596 | | 4/1992 |
| WO | WO 95/31898 | | 11/1995 |
| WO | WO 97/21792 | | 6/1997 |

* cited by examiner

Primary Examiner—S. Mark Clardy
(74) Attorney, Agent, or Firm—Keil & Weinkauf

(57) ABSTRACT

The present invention relates to an agrotechnical formulation which comprises, in each case based on the total weight of the formulation:

a) 20 to 99.9% by weight of at least one cyclohexanepolycarboxylic ester of the formula I

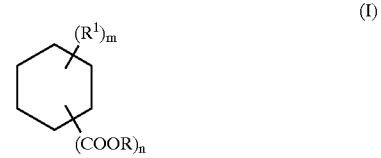

in which
$R^1$ is $C_1$–$C_{10}$-alkyl or $C_3$–$C_8$-cycloalkyl;
m is 0, 1, 2 or 3; and
n is 2, 3 or 4; and
R is H or $C_1$–$C_{30}$-alkyl, where at least one radical R is $C_1$–$C_{30}$-alkyl;

b) 0 to 70% by weight of water;
c) 0.1 to 60% by weight of at least one adjuvant and/or additive; and
d) 0 to 70% by weight of at least one active ingredient for plant treatment.

11 Claims, No Drawings

AGROTECHNICAL FORMULATION

The present invention relates to an agrotechnical formulation comprising a cyclohexanepolycarboxylic ester.

Plant treatment products are predominantly employed as liquid formulation. As a rule, this is provided as a concentrate, it being possible for the concentrate already to comprise activity-enhancing additives (built-in product). As an alternative, there exist adjuvants which can be mixed prior to use with the active ingredient, which is packaged separately, to give a tank mix (stand-alone product). As a rule, formulations of this type comprise an oil phase which frequently comprises esters of aliphatic or aromatic mono- or dicarboxylic acids for enhancing or guaranteeing the activity. Thus, WO 95/01722 describes a formulation which, besides water and a pesticide, comprises a dispersant, a wetter, a thickener and, if appropriate, an organic solvent, it being possible for the solvent to take the form of, inter alia, soya oil or rapeseed oil. WO 95/31898 describes an oil-in-water formulation comprising a solvent which is selected from among aromatic mono- and dicarboxylic esters, such as phthalic esters, fatty esters derived from vegetable oils, and aliphatic esters of adipic acid, glutaric acid and succinic acid. Phthalic esters have an estrogen-like action and are suspected of being able to lead to tumor genesis. DE 29 05 122 A discloses liquid emulsifiable herbicide formulations with linuron as active ingredient comprising dialkyl phthalates, phthalic-acid-alkyd resins, oil-modified phthalic-acid-alkyd resins or terpene phenolic resins as crystallization-inhibiting components. U.S. Pat. No. 4,834,908 describes an oil concentrate comprising a lower alkyl ester of a $C_4$–$C_{22}$-fatty acid, an anionic surfactant and a long-chain carboxylic acid. SU 537 660 describes a synergistically acting herbicide mixture which can comprise specific solvents, such as dimethyl phthalate or dibutyl phthalate, for spraying.

DE 32 47 050 A describes herbicidal compositions comprising an active ingredient and a synthetic spreading agent, which may take the form of a fatty acid ester. WO 92/06596 describes plant treatment products where the uptake and transport of the active ingredient is increased by using an adjuvant, which may take the form of, inter alia, a fatty acid ester. EP 579 052 A describes a plant treatment product comprising, inter alia, an aliphatic dicarboxylic ester for improving the penetrability into the cuticula.

DE 197 01 123 A describes a mixture comprising a dicarboxylic ester of the formula ROOC—A—COOR in which R is a $C_1$–$C_{20}$-alkyl group and A is alkylidene, alkenylidene, alkynylidene, cycloalkylidene, cycloalkenylidene or phenylene and a product which is obtained by reacting an oil or fat based on a triglyceride of $C_2$–$C_{30}$ carboxylic acids with ethylene oxide and/or propylene oxide in the presence of a base. This mixture makes it possible to reduce the application rates of plant protectants and/or to increase the spectrum of action of the plant protectants.

It is an object of the present invention to provide an agrotechnical formulation in which the application rates of active ingredient(s) and formulation auxiliaries are reduced and/or the activity is improved. Moreover, it is intended that the formulation has toxicologically and ecologically advantageous properties.

We have found that this object is achieved by using cyclohexanepolycarboxylic esters in the formulation.

The present invention therefore relates to an agrotechnical mixture or an agrotechnical formulation comprising:

a) 20 to 99.9% by weight of at least one cyclohexanecarboxylic ester of the formula I

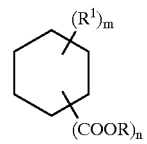

(I)

in which $R^1$ is $C_1$–$C_{10}$-alkyl or $C_3$–$C_8$-cycloalkyl;
m is 0, 1, 2 or 3;
R is $C_1$–$C_{30}$-alkyl; and
n is 2, 3 or 4.

b) 0 to 70% by weight of water;
c) 0.1 to 60% by weight of at least one adjuvant and/or additive; and
d) 0 to 70% by weight of at least one active ingredient for plant treatment.

The $C_1$–$C_{10}$- and $C_1$–$C_{30}$-alkyl groups can be straight-chain or branched. If $R^1$ is an alkyl group, this preferably takes the form of a $C_1$–$C_8$-alkyl group and, in particular, $C_1$–$C_6$-alkyl group. Examples of such an alkyl group are methyl, ethyl, n-propyl, i-propyl, n-butyl, i-butyl, sec-butyl, t-butyl, n-pentyl, n-hexyl, n-octyl, 2-ethylhexyl, and the like.

R is preferably $C_2$–$C_{20}$-alkyl and in particular $C_3$–$C_{18}$-alkyl. Examples of such alkyl groups are the alkyl groups stated above for $R^1$ and also n-nonyl, iso-nonyl, n-decyl, iso-decyl, n-undecyl, iso-undecyl, n-dodecyl, iso-dodecyl, n-tridecyl, iso-tridecyl, stearyl, n-eicosyl, and the like.

Component a):

Examples of cyclohexanepolycarboxylic esters which can be used in accordance with the invention are Alkyl cyclohexane-1,4-dicarboxylates, such as, for example, monomethyl cyclohexane-1,4-dicarboxylate, dimethyl cyclohexane-1,4-dicarboxylate, diethyl cyclohexane-1,4-dicarboxylate, di-n-propyl cyclohexane-1,4-dicarboxylate, di-n-butyl cyclohexane-1,4-dicarboxylate, di-tert-butyl cyclohexane-1,4-dicarboxylate, cyclohexane-1,4-dicarboxylic acid monoglycol ester, cyclohexane-1,4-dicarboxylic acid diglycol ester, di-n-octyl cyclohexane-1,4-dicarboxylate, diisooctyl cyclohexane-1,4-dicarboxylate, mono-2-ethylhexyl cyclohexane-1,4-dicarboxylate, di-2-ethylhexyl cyclohexane-1,4-dicarboxylate, di-n-nonyl cyclohexane-1,4-dicarboxylate, diisononyl cyclohexane-1,4-dicarboxylate, di-n-decyl cyclohexane-1,4-dicarboxylate, di-n-undecyl cyclohexane-1,4-dicarboxylate, diisodecyl cyclohexane-1,4-dicarboxylate, diisododecyl cyclohexane-1,4-dicarboxylate, di-n-octadecyl cyclohexane-1,4-dicarboxylate, diisooctadecyl cyclohexane-1,4-dicarboxylate, di-n-eicosyl cyclohexane-1,4-dicarboxylate, monocyclohexyl cyclohexane-1,4-dicarboxylate, dicyclohexyl cyclohexane-1,4-dicarboxylate;

Alkyl cyclohexane-1,2-dicarboxylates, such as, for example, monomethyl cyclohexane-1,2-dicarboxylate, dimethyl cyclohexane-1,2-dicarboxylate, diethyl cyclohexane-1,2-dicarboxylate, di-n-propyl cyclohexane-1,2-dicarboxylate, di-n-butyl cyclohexane-1,2-dicarboxylate, di-tert-butyl cyclohexane-1,2-dicarboxylate, cyclohexane-1,2-dicarboxylic acid monoglycol ester, cyclohexane-1,2-dicarboxylic acid diglycol ester, di-n-octyl cyclohexane-1,2-dicarboxylate, diisooctyl cyclohexane-1,2-dicarboxylate, di-2-ethylhexyl cyclohexane-1,2-dicarboxylate, di-n-nonyl cyclohexane-1,2-dicarboxylate, diisononyl cyclohexane-1,2-dicarboxylate, di-n-decyl cyclohexane-1,2-dicarboxylate, diisodecyl cyclohexane-1,2-dicarboxylate, di-n-undecyl cyclohexane-1,2-dicarboxylate, diisododecyl cyclohexane-1,2-dicarboxylate, di-n-octadecyl cyclohexane-1,2- dicarboxylate, diisooctadecyl cyclohexane-1,2-dicarboxylate, di-n-eicosyl cyclohexane-1,2-dicarboxylate, monocyclohexyl cyclohexane-1,2-dicarboxylate, dicyclohexyl cyclohexane-1,2-dicarboxylate;

Alkyl cyclohexane-1,3-dicarboxylates, such as, for example, monomethyl cyclohexane-1,3-dicarboxylate, dimethyl cyclohexane-1,3-dicarboxylate, diethyl cyclohexane-1,3-dicarboxylate, di-n-propyl cyclohexane-1,3-dicarboxylate, di-n-butyl cyclohexane-1,3-dicarboxylate, di-tert-butyl cyclohexane-1,3-dicarboxylate, cyclohexane-1,3-dicarboxylic acid monoglycol ester, cyclohexane-1,3-dicarboxylic acid diglycol ester, di-n-octyl cyclohexane-1,3-dicarboxylate, diisooctyl cyclohexane-1,3-dicarboxylate, di-2-ethylhexyl cyclohexane-1,3-dicarboxylate, di-n-nonyl cyclohexane-1,3-dicarboxylate, diisononyl cyclohexane-1,3-dicarboxylate, di-n-decyl cyclohexane-1,3-dicarboxylate, diisodecyl cyclohexane-1,3-dicarboxylate, di-n-undecyl cyclohexane-1,3-dicarboxylate, diisododecyl cyclohexane-1,3-dicarboxylate, di-n-octadecyl cyclohexane-1,3-dicarboxylate, diisooctadecyl cyclohexane-1,3-dicarboxylate, di-n-eicosyl cyclohexane-1,3-dicarboxylate, monocyclohexyl cyclohexane-1,3-dicarboxylate, dicyclohexyl cyclohexane-1,3-dicarboxylate.

Alkyl cyclohexane-1,2,4-tricarboxylates, such as, for example, monomethyl cyclohexane-1,2,4-tricarboxylate, dimethyl cyclohexane-1,2,4-tricarboxylate, diethyl cyclohexane-1,2,4-tricarboxylate, di-n-propyl cyclohexane-1,2,4-tricarboxylate, di-n-butyl cyclohexane-1,2,4-tricarboxylate, di-tert-butyl cyclohexane-1,2,4-tricarboxylate, diisobutyl cyclohexane-1,2,4-tricarboxylate, cyclohexane-1,2,4-tricarboxylic acid monoglycol ester, cyclohexane-1,2,4-tricarboxylic acid diglycol ester, di-n-octyl cyclohexane-1,2,4-tricarboxylate, diisooctyl cyclohexane-1,2,4-tricarboxylate, di-2-ethylhexyl cyclohexane-1,2,4-tricarboxylate, di-n-nonyl cyclohexane-1,2,4-tricarboxylate, diisononyl cyclohexane-1,2,4-tricarboxylate, di-n-decyl cyclohexane-1,2,4-tricarboxylate, diisodecyl cyclohexane-1,2,4-tricarboxylate, di-n-undecyl cyclohexane-1,2,4-tricarboxylate, diisododecyl cyclohexane-1,2,4-tricarboxylate, di-n-octadecyl cyclohexane-1,2,4-tricarboxylate, diisooctadecyl cyclohexane-1,2,4-tricarboxylate, di-n-eicosyl cyclohexane-1,2,4-tricarboxylate, monocyclohexyl cyclohexane-1,2,4-tricarboxylate, dicyclohexyl cyclohexane-1,2,4-tricarboxylate, and also trimethyl cyclohexane-1,2,4-tricarboxylate, triethyl cyclohexane-1,2,4-tricarboxylate, tri-n-propyl cyclohexane-1,2,4-tricarboxylate, tri-n-butyl cyclohexane-1,2,4-tricarboxylate, tri-tert-butyl cyclohexane-1,2,4-tricarboxylate, triisobutyl cyclohexane-1,2,4-tricarboxylate, cyclohexane-1,2,4-tricarboxylic acid triglycol ester, tri-n-octyl cyclohexane-1,2,4-tricarboxylate, triisooctyl cyclohexane-1,2,4-tricarboxylate, tri-2-ethylhexyl cyclohexane-1,2,4-tricarboxylate, tri-n-nonyl cyclohexane-1,2,4-tricarboxylate, triisododecyl cyclohexane-1,2,4-tricarboxylate, tri-n-undecyl cyclohexane-1,2,4-tricarboxylate, triisododecyl cyclohexane-1,2,4-tricarboxylate, tri-n-octadecyl cyclohexane-1,2,4-tricarboxylate, triisooctadecyl cyclohexane-1,2,4-tricarboxylate, tri-n-eicosyl cyclohexane-1,2,4-tricarboxylate, tricyclohexyl cyclohexane-1,2,4-tricarboxylate.

Alkyl cyclohexane-1,3,5-tricarboxylates, such as, for example, monomethyl cyclohexane-1,3,5-tricarboxylate, dimethyl cyclohexane-1,3,5-tricarboxylate, diethyl cyclohexane-1,3,5-tricarboxylate, di-n-propyl cyclohexane-1,3,5-tricarboxylate, di-n-butyl cyclohexane-1,3,5-tricarboxylate, di-tert-butyl cyclohexane-1,3,5-tricarboxylate, diisobutyl cyclohexane-1,3,5-tricarboxylate, cyclohexane-1,3,5-tricarboxylic acid monoglycol ester, cyclohexane-1,3,5-tricarboxylic acid diglycol ester, di-n-octyl cyclohexane-1,3,5-tricarboxylate, diisooctyl cyclohexane-1,3,5-tricarboxylate, di-2-ethylhexyl cyclohexane-1,3,5-tricarboxylate, di-n-nonyl cyclohexane-1,3,5-tricarboxylate, diisononyl cyclohexane-1,3,5-tricarboxylate, di-n-decyl cyclohexane-1,3,5-tricarboxylate, diisodecyl cyclohexane-1,3,5-tricarboxylate, di-n-undecyl cyclohexane-1,3,5-tricarboxylate, diisododecyl cyclohexane-1,3,5-tricarboxylate, di-n-octadecyl cyclohexane-1,3,5-tricarboxylate, diisooctadecyl cyclohexane-1,3,5-tricarboxylate, di-n-eicosyl cyclohexane-1,3,5-tricarboxylate, monocyclohexyl cyclohexane-1,3,5-tricarboxylate, dicyclohexyl cyclohexane-1,3,5-tricarboxylate, and also trimethyl cyclohexane-1,3,5-tricarboxylate, triethyl cyclohexane-1,3,5-tricarboxylate, tri-n-propyl cyclohexane-1,3,5-tricarboxylate, tri-n-butyl cyclohexane-1,3,5-tricarboxylate, tri-tert-butyl cyclohexane-1,3,5-tricarboxylate, triisobutyl cyclohexane-1,3,5-tricarboxylate, cyclohexane-1,3,5-tricarboxylic acid triglycol ester, tri-n-octyl cyclohexane-1,3,5-tricarboxylate, triisooctyl cyclohexane-1,3,5-tricarboxylate, tri-2-ethylhexyl cyclohexane-1,3,5-tricarboxylate, tri-n-nonyl cyclohexane-1,3,5-tricarboxylate, triisododecyl cyclohexane-1,3,5-tricarboxylate, tri-n-undecyl cyclohexane-1,3,5-tricarboxylate, triisododecyl cyclohexane-1,3,5-tricarboxylate, tri-n-octadecyl cyclohexane-1,3,5-tricarboxylate, triisooctadecyl cyclohexane-1,3,5-tricarboxylate, tri-n-eicosyl cyclohexane-1,3,5-tricarboxylate, tricyclohexyl cyclohexane-1,3,5-tricarboxylate.

Alkyl cyclohexane-1,2,3-tricarboxylates, such as, for example, monomethyl cyclohexane-1,2,3-tricarboxylate, dimethyl cyclohexane-1,2,3-tricarboxylate, diethyl cyclohexane-1,2,3-tricarboxylate, di-n-propyl cyclohexane-1,2,3-tricarboxylate, di-n-butyl cyclohexane-1,2,3-tricarboxylate, di-tert-butyl cyclohexane-1,2,3-tricarboxylate, diisobutyl cyclohexane-1,2,3-tricarboxylate, cyclohexane-1,2,3-tricarboxylic acid monoglycol ester, cyclohexane-1,2,3-tricarboxylic acid diglycol ester, di-n-octyl cyclohexane-1,2,3-tricarboxylate, diisooctl cyclohexane-1,2,3-tricarboxylate, di-2-ethylhexyl cyclohexane-1,2,3-tricarboxylate, di-n-nonyl cyclohexane-1,2,3-tricarboxylate, diisononyl cyclohexane-1,2,3-tricarboxylate, di-n-decyl cyclohexane-1,2,3-tricarboxylate, diisodecyl cyclohexane-1,2,3-tricarboxylate, di-n-undecyl cyclohexane-1,2,3-tricarboxylate, diisododecyl cyclohexane-1,2,3-tricarboxylate, di-n-octadecyl cyclohexane-1,2,3-tricarboxylate, diisooctadecyl cyclohexane-1,2,3-tricarboxylate, di-n-eicosyl cyclohexane-1,2,3-tricarboxylate, monocyclohexyl cyclohexane-1,2,3-tricarboxylate, dicyclohexyl cyclohexane-1,2,3-tricarboxylate, and also trimethyl cyclohexane-1,2,3-tricarboxylate, triethyl cyclohexane-1,2,3-tricarboxylate, tri-n-propyl cyclohexane-1,2,3-tricarboxylate, tri-n-butyl cyclohexane-1,2,3-tricarboxylate, tri-tert-butyl cyclohexane-1,2,3-tricarboxylate, triisobutyl cyclohexane-1,2,3-tricarboxylate, cyclohexane-1,2,3-tricarboxylic acid triglycol ester, tri-n-octyl cyclohexane-1,2,3-tricarboxylate, triisooctyl cyclohexane-1,2,3-tricarboxylate, tri-2-ethylhexyl cyclohexane-1,2,3-tricarboxylate, tri-n-nonyl cyclohexane-1,2,3-tricarboxylate, triisododecyl cyclohexane-1,2,3-tricarboxylate, tri-n-undecyl cyclohexane-1,2,3-tricarboxylate, triisododecyl cyclohexane-1,2,3-tricarboxylate, tri-n-octadecyl cyclohexane-1,2,3-tricarboxylate, triisooctadecyl cyclohexane-1,2,3-tricarboxylate, tri-n-eicosyl cyclohexane-1,2,3-tricarboxylate, tricyclohexyl cyclohexane-1,2,3-tricarboxylate.

Alkyl cyclohexane-1,2,4,5-tetracarboxylates, such as, for example, monomethyl cyclohexane-1,2,4,5-tetracarboxylate, dimethyl cyclohexane-1,2,4,5-tetracarboxylate, diethyl cyclohexane-1,2,4,5-tetracarboxylate, di-n-propyl cyclohexane-1,2,4,5-tetracarboxylate, di-n-butyl cyclohexane-1,2,4,5-tetracarboxylate, di-tert-butyl cyclohexane-1,2,4,5-tetracarboxylate, diisobutyl cyclohexane-1,2,4,5-tetracarboxylate, cyclohexane-1,2,4,5-tetracarboxylic acid monoglycol ester, cyclohexane-1,2,4,5-tetracarboxylic acid diglycol ester, di-n-octyl cyclohexane-1,2,4,5-tetracarboxylate, diisooctl cyclohexane-1,2,4,5-tetracarboxylate, di-2-ethylhexyl cyclohexane-1,2,4,5-tetracarboxylate, di-n-nonyl cyclohexane-1,2,4,5-tetracarboxylate, diisononyl cyclohexane-1,2,4,5-tetracarboxylate, di-n-decyl cyclohexane-1,2,4,5-tetracarboxylate, diisodecyl cyclohexane-1,2,4,5-tetracarboxylate, di-n-undecyl cyclohexane-1,2,4,5-tetracarboxylate, diisododecyl cyclohexane-1,2,4,5-tetracarboxylate, di-n-octadecyl cyclohexane-1,2,4,5-tetracarboxylate, diisooctadecyl cyclohexane-1,2,4,5-tetracarboxylate, di-n-eicosyl cyclohexane-1,2,4,5-tetracarboxylate, monocyclohexyl cyclohexane-1,2,4,5-tetracarboxylate, trimethyl cyclohexane-1,2,4,5-tetracarboxylate, triethyl cyclohexane-1,2,4,5-tetracarboxylate, tri-n-propyl cyclohexane-1,2,4,5-tetracarboxylate, tri-n-butyl cyclohexane-1,2,4,5-tetracarboxylate, tri-tert-butyl cyclohexane-1,2,4,5-tetracarboxylate, triisobutyl cyclohexane-1,2,4,5-tetracarboxylate, cyclohexane-1,2,3-tricarboxylic acid triglycol ester, tri-n-octyl cyclohexane-1,2,4,5-tetracarboxylate, triisooctyl cyclohexane-1,2,4,5-tetracarboxylate, tri-2-ethylhexyl cyclohexane-1,2,4,5-tetracarboxylate, tri-n-nonyl cyclohexane-1,2,4,5-tetracarboxylate, triisododecyl cyclohexane-1,2,4,5-tetracarboxylate, tri-n-undecyl cyclohexane-1,2,4,5-tetracarboxylate, triisododecyl cyclohexane-1,2,4,5-tetracarboxylate, tri-n-octadecyl cyclohexane-1,2,4,5-tetracarboxylate, triisooctadecyl cyclohexane-1,2,4,5-tetracarboxylate, tri-n-eicosyl cyclohexane-1,2,4,5-tetracarboxylate, tricyclohexyl cyclohexane-1,2,4,5-tetracarboxylate, and also tetramethyl cyclohexane-1,2,4,5-tetracarboxylate, tetraethyl cyclohexane-1,2,4,5-tetracarboxylate, tetra-n-propyl cyclohexane-1,2,4,5-tetracarboxylate, tetra-n-butyl cyclohexane-1,2,4,5-tetracarboxylate, tetra-tert-butyl cyclohexane-1,2,4,5-tetracarboxylate, tetraisobutyl cyclohexane-1,2,4,5-tetracarboxylate, cyclohexane-1,2,4,5-tetracarboxylic acid tetraglycol ester, tetra-n-octyl cyclohexane-1,2,4,5-tetracarboxylate, tetraisooctyl cyclohexane-1,2,4,5-tetracarboxylate, tetra-2-ethylhexyl cyclohexane-1,2,4,5-tetracarboxylate, tetra-n-nonyl cyclohexane-1,2,4,5-tetracarboxylate, tetraisododecyl cyclohexane-1,2,4,5-tetracarboxylate, tetra-n-undecyl cyclohexane-1,2,4,5-tetracarboxylate, tetraisododecyl cyclohexane-1,2,4,5-tetracarboxylate, tetra-n-octadecyl cyclohexane-1,2,4,5-tetracarboxylate, tetraisooctadecyl cyclohexane-1,2,4,5-tetracarboxylate, tetra-n-eicosyl cyclohexane-1,2,4,5-tetracarboxylate, tetracyclohexyl cyclohexane-1,2,4,5-tetracarboxylate.

The cyclohexane-1,2-dicarboxylic esters are especially preferably used, in particular the following:

Di(isopentyl) cyclohexane-1,2-dicarboxylate, obtainable by hydrogenating di(isopentyl)phthalate with the Chemical Abstracts Registry Number (hereinbelow: CAS No.) 84777-06-0;

Di(isoheptyl) cyclohexane-1,2-dicarboxylate, obtainable by hydrogenating di(isoheptyl)phthalate with the CAS No. 71888-89-6;

Di(isononyl) cyclohexane-1,2-dicarboxylate, obtainable by hydrogenating a di(isononyl)phthalate with the CAS No. 68515-48-0;

Di(isononyl) cyclohexane-1,2-dicarboxylate, obtainable by hydrogenating an n-butene-based di(isononyl)phthalate with the CAS No. 28553-12-0;

Di(isononyl) cyclohexane-1,2-dicarboxylate, obtainable by hydrogenating an isobutene-based di(isononyl)phthalate with the CAS No. 28553-12-0;

a 1,2-di-$C_9$-alkylester of cyclohexanedicarboxylic acid, obtainable by hydrogenating a di(nonyl)phthalate with the CAS No. 68515-46-8;

a di(isodecyl) cyclohexane-1,2-dicarboxylate, obtainable by hydrogenating a di(isodecyl)phthalate with the CAS No. 68515-49-1;

a 1,2-di-$C_{7-11}$-alkylester of cyclohexanedicarboxylic acid, obtainable by hydrogenating the corresponding phthalic ester with the CAS No. 68515-42-4;

a 1,2-di-$C_{7-11}$-alkylester of cyclohexanedicarboxylic acid obtainable by hydrogenating the di-$C_{7-11}$-phthalates with the following CAS Nos. 111 381-89-6, 111 381 90-9, 111 381 91-0, 68515-44-6, 68515-45-7 and 3648-20-7;

a 1,2-di-$C_{9-11}$-alkylester of cyclohexanedicarboxylic acid, obtainable by hydrogenating a di-$C_{9-11}$-phthalate with the CAS No. 98515-43-5;

a 1,2-di(isodecyl)cyclohexanedicarboxylate, obtainable by hydrogenating a di(isodecyl)phthalate, which is mainly composed of di-(2-propylheptyl)phthalate;

a 1,2-di-$C_{7-9}$-cyclohexanedicarboxylate, obtainable by hydrogenating the corresponding phthalic ester, which has branched or linear $C_{7-9}$-alkyl ester groups;

Further cyclohexanepolycarboxylic esters which can be used are the nuclear hydrogenation products of the commercially available benzenecarboxylic esters with the trade names Jayflex DINP (CAS No. 68515-48-0), Jayflex DIDP (CAS No. 68515-49-1), Palatinol 9-P, Vestinol 9 (CAS No. 28553-12-0), TOTM-I (CAS No. 3319-31-1), Linplast 68-TM and Palatinol N (CAS No. 28553-12-0).

The cyclohexanepolycarboxylic esters are known or can be prepared by known methods. They are generally prepared by subjecting the esters of the corresponding benzenepolycarboxylic acids, such as phthalic acid, isophthalic acid, terephthalic acid, trimellitic acid, hemimellitic acid, pyromellitic acid or trimesic acid, to ring hydrogenation. Ring hydrogenation methods are known to the skilled worker, for example from WO 99/32427. The content of this publication is referred to in its entirety. The esters of the benzenepolycarboxylic acids are obtained in the customary manner by reacting the alcohols with the acids or their anhydrides.

The cyclohexanepolycarboxylic esters can be used singly or in mixtures of two or more. As a rule, the abovementioned cyclohexane-1,2-dicarboxylic esters take the form of mixtures, the individual esters differing by the structure of the alcohol residue, for production reasons (the number of carbon atoms of the alcohol residues is generally identical). The cyclohexane-1,2-dicarboxylic esters are preferably prepared starting from an olefin or a mixture of isomeric olefins obtained, for example, by dimerization of an olefin. The olefin or the mixture of isomeric olefins is then subjected to a hydroformylation with CO and $H_2$ and, if appropriate, a hydrogenation to give the corresponding alcohol, which has one more carbon atom than the olefin. The alcohol is then reacted with phthalic anhydride to give the corresponding phthalic ester, which is subsequently subjected to ring hydrogenation. The abovementioned olefin dimerization, olefin formylation and olefin hydrogenation are methods which are known to the skilled worker and which are described, for example, in Ullmann's Encyclopedia of Industrial Chemistry, Vol. A13, 243 and 406 (1989) and Vol. A18 321 (1991).

Di(isononyl) cyclohexane-1,2-dicarboxylate is especially preferably used in the formulations according to the invention. The former is obtainable by butene dimerization starting from a mixture of 1-butene, iso-butene, trans-2-butene and cis-2-butene on a nickel-oxide-containing catalyst. The resulting octene mixture is subjected to hydroformylation with CO and $H_2$ using a cobalt or rhodium catalyst and subsequently to hydrogenation using a customary hydrogenation catalyst, for example Raney nickel. In this manner, a mixture of isomeric nonanoles is obtained, which is converted into di(isononyl) cyclohexane-1,2-dicarboxylate by reaction with phthalic anhydride and nuclear hydrogenation.

The amount of cyclohexanepolycarboxylic ester in the formulation according to the invention preferably amounts to 30 to 90% by weight, in particular to 40 to 80% by weight, based on the total weight of the formulation.

Component b):

The formulation according to the invention can be anhydrous or comprise 0.5 to 70% by weight of water. Preferably, the formulation comprises water, viz. in an amount of 16 to 70% by weight, in particular 20 to 70% by weight, based on the total weight of the formulation. The amount of water depends on the formulation chosen.

Component c):

The formulations according to the invention comprise customary adjuvants and/or additives for the preparation of formulations in the field of crop protection. These include, for example, surfactants, dispersants, wetters, thickeners, organic solvents, cosolvents, antifoams, carboxylic acids, preservatives, stabilizers and the like.

Examples of suitable surfactants and dispersants are:

Anionic surfactants, for example alkali, alkaline earth or ammonium salts of the fatty acids, such as potassium stearate, alkyl sulfates, alkyl ether sulfates, alkylsulfonates or iso-alkylsulfonates, alkylbenzenesulfonates such as sodium dodecylbenzenelsulfonate, alkylnaphthalenesulfonates, alkyl methyl ester sulfonates, acyl glutamates, alkylsulfosuccinates, sarcosinates such as sodium lauroyl sarcosinate or taurates, Cationic surfactants, for example alkyltrimethylammonium halides or alkyltrimethylammonium alkyl sulfates, alkylpyridinium halides or dialkyldimethylammonium halides or dialkyldimethylammonium alkyl sulfates, Nonionic surfactants, for example alkoxylated animal or vegetable fats and oils such as corn oil ethoxylates, castor oil ethoxylates, talo fat ethoxylates, glycerol esters such as glycerol monostearate, fatty alcohol alkoxylates and oxoalcohol alkoxylates, fatty acid alkoxylates such as oleic acid ethoxylates, alkylphenol alkoxylates such as isononylphenol ethoxylates, fatty amine alkoxylates, fatty acid amide alkoxylates, sugar surfactants such as sorbitan fatty acid esters (sorbitan monooleate, sorbitan tristearate), polyoxyethylene sorbitan fatty acid esters, alkyl polyglycosides, N-alkylgluconamides, alkylmethyl sulfoxides, alkyldimethylphosphine oxides such as tetradecyldimethylphosphine oxide, Zwitterionic surfactants, for example sulfobetaines, carboxybetaines, alkyldimethylamine oxides such as tetradecyldimethyl amine oxide, Polymer surfactants, for example di-, tri- or multi-block polymers of the (AB)x, ABA and BAB type, such as polyethylene oxide block polypropylene oxide, polystyrene block polyethylene oxide, AB comb polymers such as polymethacrylate comb polyethylene oxide or polyacrylate comb polyethylene oxide, Perfluoro surfactants, silicone surfactants, phospholipids such as lecithin, amino acid surfactants such as N-lauroylglutamate, surface-active homo- and copolymers such as polyvinylpyrrolidone, polyacrylic acid, polyvinyl alcohol, polyethylene oxide, maleic anhydride/isobutene copolymers, vinypyrrolidone/ vinyl acetate copolymers.

It is preferred to use, as surfactant, one or more uniform or mixed esters of phosphoric acid or diphosphoric acid with polyalkylene oxide ethers, the polyalkylene oxide ethers generally only having a single hydroxyl group (for example Klearfac®, made by BASF Corp.).

Suitable examples of polyalkylene oxide ethers are ethers of alkylphenols such as nonylphenol or of branched or unbranched aliphatic alcohols, for example having 6 to 30, preferably 10 to 20, carbon atoms and in particular of fatty alcohols having 10 to 12 carbon atoms.

The monohydroxylated polyalkylene oxide ethers are generally known or can be obtained in a manner known per se, especially by alkoxylation of the corresponding alcohols. Preferred alkoxylating agents are ethylene oxide and propylene oxide, both of which can be reacted singly, in a mixture, in succession or alternatingly with a suitable phosphorus compound, and this may result in alkoxylation products of different compositions, for example having block structures.

The preparation of these phosphoric esters is generally known and is carried out, for example, by reacting the corresponding monofunctional polyalkylene oxide ethers with phosphoric acid, diphosphorus pentoxide, polyphosphoric acid or phosphorus oxytrichloride (cf. "Nonionic Surfactants", Martin Schick (Ed.), Marcel Dekker, New York, 1964, Chapter 11, pages 372–394).

The surfactants and/or dispersants can in each case amount to 0 to 40% by weight, preferably 2 to 30% by weight, based on the total weight of the formulation.

Examples of wetters which are suitable are, in particular:

Polyoxyethylene/polyoxypropylene block polymers, for example as disclosed in U.S. Pat. No. 2,677,700, U.S. Pat. No. 2,674,619 and EP-A-298 909; especially suitable products of this group are commercially available for example under the name PLURONIC® (BASF AG), Synperonic PE types or Genapol brands;

Polyoxyethylene fatty alcohols or polyoxyethylene/ polyoxypropylene fatty alcohols (for example as disclosed in GB-A 643,422 or Satkowski et al., Ind. Eng. Chem. 49 (1957) 1875); especially suitable products of this group are commercially available for example under the name Plurafac® LF types (BASF AG);

Polyoxyethylene fatty amines or polyoxyethylene/ polyoxypropylene fatty amines, for example as known from Stache, Tensidtaschenbuch [Surfactants Guide], Carl-Hauser-Verlag Munich, Vienna, 2nd Edition, p. 133; especially suitable products of this group are commercially available for example under the names ATPLUS® (Uniqema) and ETHOMEEN® (Akzo);

Fatty acid esters or fatty acid ester ethoxylates, for example as disclosed in U.S. Pat. No. 1,914,100; especially suitable products of this group are commercially available for example under the names ARLACEL®, ATMER®, ATMOS® and ATPET®;

Polyoxyethylene oxyalcohols or polyoxyethylene/ polyoxypropylene oxyalcohols, for example as disclosed in U.S. Pat. No. 2,508,035, U.S. Pat. No. 2,508, 036, U.S. Pat. No. 2,617,830; especially suitable products of this group are commercially available for example under the names LUTENSOL AT®, AO®, ON®, and LUTENSOL TO® (BASF AG);

Polyoxyethylene alkylphenols or polyoxyethylene/ polyoxypropylene alkylphenols, for example as disclosed in FR-A 842 943; especially suitable products of this group are commercially available for example under the name LUTENSOL AP® (BASF). Furthermore, for example also polyethlyene glycol (PEG) alkyd resins, such as, for example, Atlox 4914 (by Uniqema) or for example a polyhydroxystearic acid/polyethylene oxide block polymer (ABA type), for example Atlox 4912 (also by Uniqema).

Furthermore also unless already otherwise stated above:

fatty acid polyoxyethylene esters such as lauryl alcohol polyoxyethylene ether acetate, alkyl polyoxyethylene ethers or alkyl polyoxypropylene ethers, for example of isotridecyl alcohol and fatty acid alcohol polyoxyethylene ethers, alkylaryl alcohol polyoxyethylene ethers such as octylphenol polyoxyethylene ether, tributylphenol polyoxyethylene ether, ethoxylated isooctylphenol, octylphenol or nonylphenol or castor oil, sorbitol esters, arylsulfonic acids, alkylsulfonic acids, alkylsulfuric acids, alkali, alkaline earth and ammonium salts of arylsulfonic acids, for example lignin-, phenol-, naphthaline- and dibutylnaphthaline sulfonic acids, alkylsulfonic acids, alkylarylsulfonic acids, alkylsulfuric acids, lauryl ether sulfuric acids and fatty alcohol sulfuric acids, fatty acids, sulfated hexa-, hepta- and octadecanols and fatty alcohol glycol ethers, condensates of sulfonated naphthaline and its derivatives with formaldehyde, condensates of naphthaline sulfonic acids with phenol and formaldehyde, and protein hydrolyzates.

The wetters can amount to 0 to 40, preferably 2 to 30% by weight in the formulation.

Suitable antifoams are aliphatic or aromatic monoalcohols having 4 to 14, preferably 6 to 10, carbon atoms, such as n-octanol or n-decanol, or silicone oil emulsions, or silicone oils and/or their derivatives.

Usually, the antifoams amount to 0.01 to 5 and especially 0.1 to 3% by weight in the formulation.

Examples of suitable organic solvents and cosolvents are mineral oils, naturally occurring oils such as rapeseed oil, soya oil and the methyl esters of the carboxylic acids on which these oils are based, such as methyl oleate and rapeseed oil methyl ester, fatty acid esters, especially with $C_1$–$C_4$-alkanols, and organic solvents such as benzenes or naphthalines which are substituted by straight-chain or branched alkyl groups (Shellsol 150R, Shellsol 200R and Solvesso® brands), aliphatic hydrocarbons such as cyclohexane or paraffins, alcohols such as butanol or glycol or their ethers and esters, ketones such as acetone, methyl ethyl ketone, methyl isobutyl ketone or cyclohexanone, polar solvents, for example amides such as dimethylformamide, N-methylpyrrolidone or N-octylpyrrolidone, or dimethyl sulfoxide.

The solvents and/or cosolvents can amount to 0 to 60 and especially 5 to 30% by weight in the formulation.

In addition, the mixture can comprise one or more carboxylic acids with 4 to 20, in particular 6 to 18 carbon atoms such as oleic acid or 2-ethylhexanoic acid and/or one or more of the dicarboxylic acids on which the compounds I are based, for example adipic acid, sebacic acid, succinic acid or fruit acids such as, for example, citric acid.

These mono- or polycarboxylic acids amount to 0 to 30, preferably 0 to 10% by weight in the formulation.

Suitable thickeners are, in particular, thixotropic additives, which impart pseudoplastic flow characteristics to the formulation, i.e. high viscosity in the state of rest and low viscosity in the state of movement. Examples of suitable compounds are polysaccharides, such as xanthan gum, Kelzan by Kelco or Rhodopol 23 by Rhone Poulenc. The thickeners are employed in an amount of 0.01 to 5% by weight, preferably 0.05 to 3% by weight and in particular 0.1 to 2% by weight based on the total weight of the formulation.

Preservatives which can be employed are customary compounds such as alkyl para-hydroxybenzoates and bacteriosides such as Proxel (commercial product by ICI), Nipacide BIT 20 (commercial product by Thor-Chemie), Kathon MK and Acticide (commercial products by Rohm & Haas). Stabilizers which can be used are organic acids, such as acetic acid or citric acid. In general, the preservative or stabilizer amounts in each case to 0 to 5% by weight, preferably 0.1 to 4% by weight, in the formulation.

Component d):

The mixtures or formulations according to the invention can be formulated without active ingredient for the treatment of plants. In this case, they take the form of stand-alone products, i.e. the mixture or the formulation and the active ingredient(s) for the treatment of plants, are sold to the user in separate packages. The advantage for the user is that he can choose the dosage of the active ingredient quantity, or active ingredient quantities, and that residues of the mixture or the formulation can also be used somewhere else.

The formulations according to the invention can also comprise at least one active ingredient for the treatment of plants, in which case they are present as built-in products. In this case, the amount of active ingredient is preferably in the range of 2 to 70% by weight, in particular 5 to 60% by weight, based on the total weight of the formulation. The active ingredient can be selected from among herbicides, fungicides, insecticides, akaricides, nematicides, and plant growth regulators.

The herbicidal crop protection products comprise one or more herbicidal plant protectants, for example from among the following:

1,3,4-Thiadiazoles such as buthidazole and cyprazole, amides such as allidochlor, benzoylpropethyl, bromobutide, chlorthiamid, dimepiperate, dimethenamid, diphenamid, etobenzanid, flamprop-methyl, fosamin, isoxaben, monalide, naptalame, pronamid, propanil, amino phosphoric acids such as bilanafos, buminafos, glufosinate-ammonium, glyphosate, sulfosate, aminotriazoles such as amitrole, anilides such as anilofos, mefenacet, aryloxyalkanoic acids such as 2,4-D, 2,4-DB, clomeprop, dichlorprop, dichlorprop-P, dichlorprop-P, fenoprop, fluroxypyr, MCPA, MCPB, mecoprop, mecoprop-P, napropamide, napropanilide, triclopyr, benzoic acids such as chloramben, dicamba, benzothiadiazinones such as bentazone, bleachers such as clomazone, diflufenican, fluorochloridone, flupoxam, fluridone, pyrazolate, sulcotrione, carbamates such as carbetamide, chlorbufam, chlorpropham, desmedipham, phenmedipham, vernolate, quinoline carboxylic acids such as quinclorac, quinmerac, dichloropropionic acids such as dalapon, dihydrobenzofurans such as ethofumesate, dihydrofuran-3-ones such as flurtamone, dinitroanilines such as benefin, butralin, dinitramin, ethalfluralin, fluchloralin, isopropalin, nitralin, oryzalin, pendimethalin, prodiamine, profluralin, trifluralin, dinitrophenols such as bromofenoxim, dinoseb, dinoseb acetate, dinoterb, DNOC, minoterb acetate, diphenyl ethers such as acifluorfen sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen, oxyfluorfen, dipyridyls such as cyperquat, difenzoquat methylsulfate, diquat, paraquat dichloride, imidazoles such as isocarbamid, imidazolinones such as imazamethapyr, imazapyr, imazaquin, imazethabenz-methyl, imazethapyr, oxadiazoles such as methazole, oxadiargyl, oxadiazon, oxiranes such as tridiphane, phenols such as bromoxynil, ioxynil, phenoxyphenoxypropionic esters such as clodinafop, cyhalofop-butyl, diclofop methyl, fenoxaprop ethyl, fenoxaprop-p-ethyl, fenthiapropethyl, fluazifop butyl, fluazifop-p-butyl, haloxyfop ethoxyethyl, haloxyfop methyl, haloxyfop-p-methyl, isoxapyrifop, propaquizafop, quizalofop ethyl, quizalofop-p-ethyl, quizalofop-tefuryl, phenylacetic acids such as chlorfenac, phenylpropionic acids such as chlorphenprop-methyl, ppi active ingredients such as benzofenap, flumiclorac-pentyl, flumioxazin, flumipropyn, flupropacil, pyrazoxyfen, sulfentrazone, thidiazimine, pyrazols such as nipyraclofen, pyridazines such as chloridazon, maleic hydrazide, norflurazon, pyridate, pyridinecarboxylic acids such as clopyralid, dithiopyr, picloram, thiazopyr, pyrimidyl ethers such as pyrithiobac-acid, pyrithiobac-sodium, KIH-2023, KIH-6127, sulfonamides such as flumetsulam, metosulam, triazolecarboxamides such as triazofenamid, uraciles such as bromacil, lenacil, terbacil, furthermore benazolin, benfuresate, bensulide, benzofluor, butamifos, cafenstrole, chlorthal-dimethyl, cinmethylin, dichlobenil, endothall, fluorbentranil, mefluidide, perfluidone, piperophos.

Preferred herbicidal plant protectants are those of the sulfonylurea type, such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl.

Herbicidal plant protectants which are furthermore preferred are those of the cyclohexenone type, such as alloxydim, clethodim, cloproxydim, cycloxydim, sethoxydim and tralkoxydim.

Very especially preferred herbicidal plant protectants of the cyclohexenone type are: tepraloxydim (cf. AGROW, No. 243, 3.11.95, page 21, caloxydim) and 2-(1-[2-{4-chlorophenoxy}propyloxyimino]butyl)-3-hydroxy-5-(2H-tetrahydrothiopyran-3-yl)-2-cyclohexen-1-one, and very especially preferred herbicidal plant protectants of the sulfonylurea type are: N-(((4-methoxy-6-[trifluoromethyl]-1,3,5-triazin-2-yl)amino) carbonyl)-2-(trifluoromethyl) benzenesulfonamide.

The fungicidal compositions comprise one or more fungicidal active ingredients, for example one or more of the following: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

Nitro derivatives such as dinitro-(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate;

Heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminomethyl benzimidazole, 2-(fur-2-yl)benzimidazole, 2-(thiazol-4-yl) benzimidazole, N-(1,1,2,2-tetrachloroethylthio) tetrahydrophthalimide, N-trichloromethylthiotetrahydrophthalimide, N-trichloromethylthiophthalimide, N-Dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridin 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxcyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-buta none, 1-(4-chlorophenoxy)-3,3-dimethyl-1-(1H-1,2,4-triazol-1-yl)-2-buta nole, (2RS,3RS)-1-[3-(2-chlorophenyl)-2-(4-fluorophenyl)oxiran-2-yl-methyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido) benzene, 1,2-bis-(3-methoxycarbonyl-2-thioureido) benzene, Strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, methyl E-methoxyimino-[α-(2-phenoxyphenyl)] acetamide, methyl E-methoxyimino-[α-(2,5-dimethylphenoxy)-o-tolyl]acetamide, Anilinopyrimidines such as N-(4,6-dimethylpyrimidin-2-yl)anilin, N-[4-methyl-6-(1-propinyl)pyrimidin-2-yl]anilin, N-[4-methyl-6-cyclopropylpyrimidin-2-yl]anilin, Phenylpyrroles such as 4-(2,2-difluoro-1,3-benzodioxol-4-yl)pyrrole-3-carbonitrile, Cinnamides such as 3-(4-chlorophenyl)-3-(3,4-dimethoxyphenyl)acryloylmorpholine,
and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine 2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluormethyl-3-chloro-2-aminopyridine, 1-((bis-(4-fluorophenyl)methylsilyl)methyl)-1H-1,2,4-triazole.

Growth regulators which can be used are, for example, the group of the gibberellins. These include, for example, the gibberellins $GA_1$, $GA_3$, $GA_4$, $GA_5$ and $GA_7$ and the like and the corresponding exo-16,17-dihydrogibberellins and their derivatives, for example the esters with $C_1$–$C_4$-carboxylic acids. Preferred in accordance with the invention is exo-16, 17-dihydro-$GA_5$-13-acetate.

The formulations according to the invention can be present as emulsifiable concentrate (EC), suspoemulsion (SE), oil-in-water emulsion (O/W), water-in-oil emulsion (W/O), aqueous suspension concentrate, oil suspension concentrate (SC), microemulsion (ME), and the like. The formulations take the form of aqueous or nonaqueous liquid formulations, the cyclohexanepolycarboxylic esters acting as solvents for the organic constituents, in particular the active ingredients, or as inert diluents. Anhydrous formulations have the advantage that, owing to the aprotic character of the cyclohexanepolycarboxylic esters, even those active ingredients can be employed where there is the risk of hydrolytic degradation upon storage in the case of aqueous formulations.

Besides the active ingredients, emulsifiable concentrates comprise an oil phase which is formed at least in part by the cyclohexanepolycarboxylic ester. The oil phase can also comprise further solvents and cosolvents as mentioned in connection with the oil SC formulations. Furthermore, the emulsifiable concentrates generally comprise emulsifiers and adjuvants such as stabilizers, antifoams and the like. In general, the cyclohexanepolycarboxylic ester is present in an amount of from 0.1 to 40% by weight, preferably 1 to 20% by weight, based on emulsifiable concentrate. The emulsifiable concentrates are prepared in the customary manner by mixing the constituents homogeneously. If appropriate, the active ingredients or adjuvants can be used as liquid preconcentrates in suitable solvents.

In the case of aqueous suspension concentrates, a water-soluble active ingredient is suspended in water at a high concentration. In general, they comprise 40 to 80% by weight of active ingredient, 0.5 to 2% by weight of wetter, 2 to 5% by weight of dispersant and, if appropriate, 0.1 to 1% by weight of thickener, based on the total weight of the formulation. For their preparation, a procedure is generally followed in which the active ingredient, which is ground to a mean particle size of approximately 1 to 5 mm, is dispersed in the mixture of the remaining components with the aid of customary methods. Approximately 1 to approximately 10% by weight (based on the total weight of the formulation) of cyclohexanepolycarboxylic ester is incorporated before or after dispersion of the active ingredient.

Oil SC formulations generally comprise 10 to 70% by weight, in particular 30 to 60% by weight, of at least one active ingredient, 10 to 85% by weight, in particlar 20 to 60% by weight, of a largely anhydrous oil phase (up to a maximum of 1% by weight of water), and 5 to 40% by weight, in particular 7.5 to 25% by weight, of at least one surfactant, in particular of an anionic surfactant, and, if appropriate, further adjuvants (in each case based on the total weight of the formulation). The active ingredient is distributed in the oil phase in finely disperse form. The oil phase is formed at least in part by the cyclohexanepolycarboxylic ester. In general, the oil phase comprises 20 to 100% by weight, in particular 40 to 100% by weight, of cyclohexanepolycarboxylic ester. If the oil phase comprises 100% by weight of cyclohexanecarboxylic ester, it can additionally comprise at least one of the following constituents:

a) a $C_8$- to $C_{30}$-hydrocarbon of the n- or iso-alkane series or a mixture of these. Examples of such hydrocarbons are n- and iso-octane, -decane, -hexadecane, -octadecane, -eicosane, and preferably hydrocarbon mixtures such as liquid paraffin (which, if technical-grade, may comprise up to approximately 5% of aromatics) and a $C_{18}$–$C_{24}$-mixture, which is commercially available from Exxon under the name Spraytex oil.

b) Aromatic or cycloaliphatic $C_7$- to $C_{18}$-hydrocarbon compounds or a mixture of these. They include, in particular, aromatic or cycloaliphatic solvents from the series of the alkyl-aromatics; the compounds can be unhydrogenated, partially hydrogenated or fully hydrogenated. These solvents of component b) include, in particular, mono-, di- or trialkylbenzenes, mono-, di-, or trialkyl-substituted tetralins and/or mono-, di-, tri- or tetraalkyl-substituted naphthalines (alkyl is preferably $C_1$–$C_6$-alkyl). Examples of such solvents are toluene, o-, m-, p-xylene, ethylbenzene, isopropylbenzene, tert-butylbenzene and mixtures, as the Exxon-products sold under the name Shellsol and Solvesso, for example Solvesso 100, 150 and 200.

c) an aliphatic ester which is selected in particular from among the group consisting of aliphatic esters, araliphatic esters and natural fats and oils, and derivatives and mixtures of these. Suitable substances are esters of aliphatic, saturated or unsaturated $C_1$–$C_{20}$-mono- and $C_2$–$C_{20}$-dicarboxylic acids with $C_1$–$C_{20}$-alkanols and phenyl-$C_1$–$C_{20}$-alkanols, the total of the carbon atoms being at least 8. Also suitable are esters of aromatic mono- and dicarboxylic acids, such as benzoic acid and phthalic acid, with $C_1$–$C_{20}$-alkanols and phenyl-$C_1$–$C_{20}$-alkanols. Preferred are methyl oleate, di-n-octyl and isooctyl adipate, octyl laurate, 2-ethylhexyl 2-ethylhexonoate, methyl oleate, n-butyl stearate, di-n-butyl adipate, di-n-nonyl and isononyl adipate, rapeseed oil methyl and ethyl ester, n-butyl benzoate, benzyl benzoate and the like.

The abovementioned natural or unprocessed fats or oils or derivatives of these (modified natural fats or oils) include, for example, materials such as soya oil, sunflower oil, rapeseed oil, corn oil and their raffinates.

To prepare oil SC formulations, solid active ingredients are ground with wetters and dispersants and, if appropriate, further adjuvants or additives in suitable devices to a mean particle size of $\leq 10$ μm. To this end, customary devices are used, such as bowl mills or stirred bowl mills together with milling elements, for example milling elements made of glass, minerals or metals. A particularly suitable device is the Dyno-mill by Bachofen, which allows to carry out the passage process. After, as a rule, 5 passages (the slurry being pumped through the mill with the aid of a roller pump), mean particle sizes in the region of 1 to 10 μm are generally achieved. Grinding is generally carried out at a temperature in the range of 0 to 30° C.

The cyclohexanepolycarboxylic esters together with the other components are subsequently stirred into the resulting oil SC preconcentrate. To this end, customary devices are used, such as conventional mixers and dispersers, in particular annular mills of the rotor-stator type.

In the case of oil SC formulations, the cyclohexanepolycarboxylic ester serves to enhance the activity and, in the case of aqueous SC formulations, to stabilize the formulation.

Suspoemulsions comprise both a solid and a liquid active ingredient dispersed in an aqueous phase. The liquid active ingredient may also be a solution of an oil-soluble active ingredient in an oil phase. In accordance with the invention, the cyclohexanepolycarboxylic ester constitutes at least part of this oil phase. In addition to the cyclohexanepolycarboxylic ester, the oil phase may also comprise at least one of the oil components mentioned above in connection with oil SC formulations.

Suspoemulsions generally comprise 30 to 60% by weight of active ingredients (total active ingredients), 1 to 20% by weight of an oil phase, 2 to 10% by weight of wetters and dispersants, 0.1 to 0.5% by weight of antifoam, 0.1 to 5% by weight of thickener and, if appropriate, further adjuvants, in each case based on the total weight of the suspoemulsion. The aqueous phase counts for the remainder of the formulation.

The active ingredient which is present in solid form in the suspoemulsion must be essentially insoluble in the oil phase and in the aqueous phase. In contrast, the active ingredient dissolved in the oil phase must be essentially insoluble in the aqueous phase.

In general, suspoemulsions are prepared starting from the SC preconcentrates. The SC preconcentrates are typically adjusted rheologically by adding thickeners. A further oil phase with at least one further active ingredient is subsequently incorporated. This is done in the customary manner, for example by vigorously stirring or by using dissolvers or annular mills.

In the case of the O/W and the W/O emulsions, the cyclohexanepolycarboxylic esters form at least part of the oil phase. Such emulsions generally comprise 20 to 60% by weight of active ingredient, 1 to 10% by weight of emulsifiers, 0.1 to 0.5% by weight of antifoams, 0.1 to 5% by weight of thickeners and, if appropriate, further adjuvants, in each case based on the total weight of the emulsion.

To prepare emulsions (O/W, W/O emulsions or multiple fluid formulations), separate preconcentrates of aqueous and nonaqueous phases are first prepared. The viscosity of the aqueous phases is generally increased by adding thickeners. The oil phase is subsequently incorporated into the aqueous phase or the aqueous phase is subsequently incorporated into the oil phase, using severe shear. To achieve the severe shear, the mixture is stirred vigorously, or shearing apparatuses, such as rotor-stator mills or aperture plates. Normally, pressure differentials may also be exploited in order to obtain high proportions of fine particles and storage-stable formulations.

In the case of microemulsions, an oil phase with a mean particle size in the range of 1 to 50 nm is dispersed in an aqueous phase. The oil phase is formed at least in part by the cyclohexanepolycarboxylic ester. In addition, the oil phase may also comprise the oil components stated above in connection with oil SC formulations. The active ingredient (s) are dissolved in the oil phase. In general, the microemulsions comprise 20 to 70% by weight of oil phase (including the active ingredient), 0.5 to 30% by weight of surfactants, 0.1 to 20% by weight of cosurfactants, 30 to 70% by weight of water and, if appropriate, further adjuvants, in each case based on the total weight. Microemulsions form spontaneously upon mixing of the components. However, it is expedient to mix the oil phase with the surfactants and cosurfactants and then to slowly mix the aqueous phase into the product.

In the case of EC and ME formulations, the formulations according to the invention can be provided as stand-alone products, i.e. the active ingredient (if appropriate together with some of the remaining components) and the remaining components are sold to the consumer in separately packaged form. This has the advantage that the quantity of active ingredient can be chosen as desired. Before they are used, the crop protection products according to the invention are processed by the user, generally the farmer, with water in a manner known per se to give the finished spray mixture. In particular, the parts of the combipack are first mixed for this purpose, and the resulting herbicidal composition is subsequently diluted with water to the desired concentration.

Normally, the sprayable mixtures comprise 0.0001 to 10, preferably 0.001 to 1, and in particular 0.01 to 0.5% by weight of the plant protectant and 0.001 to 50, preferably 0.01 to 5 and in particular 0.1 to 0.5% by weight of the mixture according to the invention.

The spray mixtures can be applied in a manner know per se, especially by spraying with a mobile sprayer using nozzles for ultra-fine distribution. The skilled worker is familiar with the equipment and techniques furthermore required for doing this.

The advantage of the formulations according to the invention is that the application rates of active ingredients and formulation auxiliaries are reduced and the activity is improved. Moreover, the cyclohexanepolycarboxylic esters are advantageous with regard to their toxicology. Experiments have shown that, in contrast to customary polycarboxylic esters, they lead to no biologically significant proliferation of peroxisomes. Moreover, the cyclohexanepolycarboxylic esters are low-odor and their odor is not offensive.

The examples which follow illustrate the invention without imposing any limitation. A di(isononyl) cyclohexane-1, 2-dicarboxylate, whose alcohol component had been obtained by butene dimerization, hydroformylation and hydration by the process stated hereinbelow, was used for the examples:

1) Butene Dimerization

The butene dimerization was carried out continuously in an adiabatic reactor composed of two separate reactors (length: 4 m each, diameter: 80 cm each) with intermediate cooling at 30 bar. The starting material used was a raffinate II of the following composition:

| Isobutane | 2% by weight |
|---|---|
| n-Butane | 10% by weight |
| iso-Butene | 2% by weight |
| 1-Butene | 32% by weight |
| trans-2-Butene | 37% by weight |
| cis-2-Butene | 17% by weight |

The catalyst used was a catalyst in accordance with DE-A 43 39 713, composed of 50% by weight NiO, 12.5% by weight $TiO_2$, 33.5% by weight $SiO_2$ and 4% by weight $Al_2O_3$ in the form of 5×5 mm tablets. The reaction was carried out with a throughput of 0.375 kg of raffinate II/l catalyst·h, a recirculation ratio of unreacted $C_4$-hydrocarbons to fresh raffinate II of 3, an intake temperature at reactor 1 of 38° C. and an intake temperature at reactor 2 of 60° C. The conversion rate based on the butenes present in raffinate II was 83.1%. The octene fraction was separated from unreacted raffinate II and the high-boiling components by fractional distillation of the reactor discharge.

2) Hydroformylation and Hydrogenation 750 g of the octene mixture prepared as described in 1) were reacted batchwise in an autoclave with 0.13% by weight of dicobalt octacarbonyl ($Co_2(CO)_8$) as catalyst with addition of 75 g of water at 185° C. and under a synthesis gas pressure of 280 bar at a mixing ratio of $H_2$ to CO of 60:40 5 h. The consumption of synthesis gas, which can be seen from a pressure drop in the autoclave, is compensated for by injecting more gas. After the pressure in the autoclave had been released, the reaction material was freed oxidatively from the cobalt catalyst using 10% by weight of acetic acid and passing in air, and the organic product phase was hydrogenated for 10 hours with Raney nickel at 125° C. and a hydrogen pressure of 280 bar. The isononanol fraction was separated from the $C_8$-paraffins and the high-boiling components by fractional distillation of the reaction material.

The composition of the isononanol fraction was analyzed by gas chromatography. Previously, a sample was trimethylsilylated for 60 minutes at 80° C. with 1 ml of N-methyl-N-trimethylsilyltrifluoroacetamide per 100 ml of sample. A separating column of the Hewlett Packard Ultra 1 50 m in length, an internal diameter of 0.32 mm and a film thickness of 0.2 μm was employed. The injector and detector temperatures were 250° C., while the oven temperature was 120° C. The split was 110 ml/min. The carrier gas was nitrogen. The pre-pressure had been set to 200 kPa. 1 ml of the sample was injected and detected by means of FID. In this way, the following sample composition was determined (gas chromatography percentage areas):

| | |
|---|---|
| 11.0% | 1-nonanol |
| 20.8% | 6-methyl-l-octanol |
| 20.5% | 4-methyl-l-octanol |
| 5.3% | 2-methyl-l-octanol |
| 11.0% | 2,5-Dimethyl-l-heptanol |
| 8.7% | 3-ethyl-l-heptanol |
| 6.2% | 4,5-Dimethyl-l-heptanol |
| 2.9% | 2-ethyl-1-heptanol |
| 2.8% | 2,3-Dimethyl-l-heptanol |
| 3.0% | 2-ethyl-4-methyl-l-hexanol |
| 2.7% | 2-propyl-l-hexanol |
| 1.6% | 3-ethyl-4-methyl-hexanol |
| Remainder to 100% | other alkanols with 9 carbon atoms. |

Measurements revealed a density of this nonanol mixture of 0.8326 at 20° C. and a refractive index $n_D^{20}$ of 1.4353. The boiling range was 204 to 209° C. under atmospheric pressure.

EXAMPLE 1

Preparation of an Aqueous Suspension Concentrate 300 g of water, 80 g of propylene glycol, 25 g of Wettol Dl (sodium salt of a condensate of phenolsulfonic acid, urea and formaldehyde; BASF AG), 50 g of Pluronic PE 10500 (propylene oxide/ethylene oxide block polymer; BASF AG) and 500 g of epoxiconazol are mixed. The mixture is ground in a stirred bowl mill until 80% of the particles have the size of <2 μm. 1 g of Silicon SRE (antifoam; Wacker Chemie), 1 g of Kathon MK (preservative based on 4-isothiazolin-3-one; Rohm & Haas) and 2.5 g of xanthan gum are subsequently added. The mixture is made up to 1000 ml with water, stirred for another 3 hours and screened through a 150 μm screen. This gives a premix concentrate with 500 g/l epoxiconazole.

390 ml of water are added to 250 ml of this concentrate, and a mixture of 250 g of the above cyclohexanedicarboxylic ester together with 10 g of Atlox 4914 (polyoxyethylene alkyl ether; Uniquema) and 20 g of Atlas G500 (modified polyester surfactant; Uniquema) are added to the mixture with stirring. Complete emulsification of the organic phase is achieved by passage over a rotor-stator mill (PUC mill). 100% of the particles of the resulting dispersion have a size of <16 μm. The dispersion is storage-stable (4-week rapid storage test at 50° C.).

EXAMPLE 2

Preparation of a Suspension Concentrate

Similarly to example 1, 1280 ml of water and a mixture of 167 g of the above cyclohexanedicarboxylic ester, 250 g of ethylene oxide/propylene oxid block copolymer (Pluronic 6400; BASF AG), 10 g of Atlox 4914 and 20 g of Atlas G5000 are added to 250 ml of the premix concentrate. The components are mixed by stirring and the resulting dispersion is homogenized by passage through a rotor-stator mill (PUC mill). 100% of the particles of the resulting dispersion have a size of <9 μm. The dispersion is storage-stable (4-week rapid storage test at 50° C.).

EXAMPLE 3

Preparation of a Suspoemulsion 250 g of fenpropimorph, 67 g of ethylene oxide/propylene oxide block copolymer (Pluronic 10500; BASF AG) and 30 g of the above cyclohexanedicarboxylic ester are mixed. The mixture is stirred together with 264 ml of the premix concentrate as described in example 1), 430 ml of water, 15 g of Wettol Dl and 10 g of Pluronic PE10500. After a single passage through a rotor-stator mill (PUC mill), a stable suspoemulsion is obtained (4-week rapid storage test at 50° C.).

We claim:

1. An agrotechnical formulation comprising, in each case based on the total weight of the formulation,
   a) 20 to 99.9% by weight of at least one cyclohexanepolycarboxylic ester of the formula I

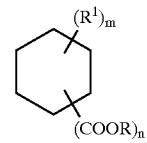

(I)

in which
   $R^1$ is $C_1$–$C_{10}$-alkyl or $C_3$–$C_8$-cycloalkyl;
   m is 0, 1, 2 or 3; and
   n is 2, 3 or 4; and
   R is H or $C_1$–$C_{30}$-alkyl, where at least one radical R is $C_1$–$C_{30}$-alkyl;

b) 0 to 70% by weight of water;
c) 0.1 to 60% by weight of at least one adjuvant and/or additive; and
d) 2 to 70% by weight of at least one active ingredient for plant treatment, with the proviso that products obtainable by reacting an oil or fat based on a triglyceride of carboxylic acids having 2 to 30 carbon atom with ethylene oxide and/or propylene oxide in the presence of bases are not present in the formulation.

2. The formulation defined in claim 1, wherein (a) is di(isononyl) cyclohexane-1,2-dicarboxylate or is a combination of di(isononyl) cyclohexane-1,2-dicarboxylate and at least one further cyclohexanepolycarboxylic ester of formula I.

3. A formulation as claimed in claim 1, comprising 16 to 70% by weight of water.

4. A formulation as claimed in claim 1, where the cyclohexanepolycarboxylic ester is selected from among ring-hydrogenated mono- and di-$C_1$–$C_{30}$-alkyl esters of phthalic acid, isophthalic acid and terephthalic acid, ring-hydrogenated mono-, di- and tri-$C_1$–$C_{30}$-alkyl esters of trimellitic acid, trimesic acid and hemimellitic acid, and ring-hydrogenated mono-, di-, tri- and tetra-$C_1$–$C_{30}$-alkyl esters of pyromellitic acid.

5. A formulation as claimed in claim 4, where the cyclohexanepolycarboxylic ester is selected from among:

Di(isopentyl) cyclohexane-1,2-dicarboxylate, obtainable by hydrogenating di(isopentyl)phthalate with the Chemical Abstracts Registry Number (hereinbelow: CAS No.) 84777-06-0;

Di(isoheptyl) cyclohexane-1,2-dicarboxylate, obtainable by hydrogenating di(isoheptyl)phthalate with the CAS No. 71888-89-6;

Di(isononyl) cyclohexane-1,2-dicarboxylate, obtainable by hydrogenating a di(isononyl)phthalate with the CAS No. 68515-48-0;

Di(isononyl) cyclohexane-1,2-dicarboxylate, obtainable by hydrogenating an n-butene-based di(isononyl) phthalate with the CAS No. 28553-12-0;

Di(isononyl) cyclohexane-1,2-dicarboxylate, obtainable by hydrogenating an isobutene-based di(isononyl) phthalate with the CAS No. 28553-12-0;

a 1,2-di-$C_9$-alkylester of cyclohexanedicarboxylic acid, obtainable by hydrogenating a di(nonyl)phthalate with the CAS No. 68515-46-8;

a di(isodecyl) cyclohexane-1,2-dicarboxylate, obtainable by hydrogenating a di(isodecyl)phthalate with the CAS No. 68515-49-1;

a 1,2-di-$C_{7-11}$-alkylester of cyclohexanedicarboxylic acid, obtainable by hydrogenating the corresponding phthalic ester with the CAS No. 68515-42-4;

a 1,2-di-$C_{7-11}$alkylester of cyclohexanedicarboxylic acid, obtainable by hydrogenating the di-$C_{7-11}$-phthalates with the following CAS Nos.: 111 381-89-6, 111 381 90-9, 111 381 91-0, 68515-44-6, 68515-45-7 and 3648-20-7;

a 1,2-di-$C_{9-11}$-alkylester of cyclohexanedicarboxylic acid, obtainable by hydrogenating a di-$C_{9-11}$-phthalate with the CAS No. 98515-43-5;

a di(isodecyl) cyclohexanedicarboxylate, obtainable by hydrogenating a di(isodecyl)phthalate, which is mainly composed of di-(2-propylheptyl)phthalate;

a 1,2-di-$C_{7-11}$-alkylester of cyclohexanedicarboxylic acid, obtainable by hydrogenating the corresponding phthalic ester which has branched or linear $C_{7-9}$-alkyl ester groups.

6. A formulation as claimed in claim 4, comprising, as cyclohexanepolycarboxylic ester, a di(isononyl) cyclohexane-1,2-dicarboxylate.

7. An agrotechnical formulation comprising, in each case based on the total weight of the formulation, a) 20 to 99.9% by weight of at least one cyclohexanepolycarboxylic ester of the formula I

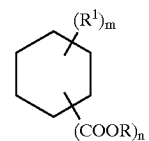

(I)

in which
$R^1$ is $C_1$–$C_{10}$-alkyl or $C_3$–$C_8$-cycloalkyl;
m is 0, 1, 2 or 3;
n is 2, 3 or 4; and
R is H or $C_1$–$C_{30}$-alkyl, where at least one radical R is $C_1$–$C_{30}$-alkyl;

b) 0 to 70% by weight of water;

c) 0.1 to 60% by weight of at least one adjuvant and/or additive, where non-ionic surfactants are selected from among glycerol esters, fatty alcohol alkoxylates and oxo-alcohol alkoxylates, alkylphenolalkoxylates; fatty aminealkoxylates, fatty acid amide alkoxylates, sugar surfactants, polyoxyethylene sorbitan fatty acid esters, alkyl polyglycosides, N-alkylgluconamides, alkylmethyl sulfoxides and alkyldimethylphosphine oxides; and d) 2 to 70% by weight of at least one active ingredient for plant treatment.

8. A method for preparing an agrotechnical formulation which comprises mixing i) at least one formulation auxiliary and
ii) an effective amount of di(isononyl) cyclohexane-1,2-dicarboxylate, optionally in combination with at least one further cyclohexanepolycarboxylic ester of formula I

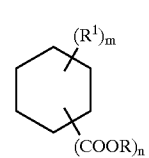

(I)

in which
$R^1$ is $C_1$–$C_{10}$-alkyl or $C_3$–$C_8$-cycloalkyl;
m is 0, 1, 2 or 3; and
n is 2, 3 or 4; and
R is H or $C_1$–$C_{30}$-alkyl, where at least one radical R is $C_1$–$C_{30}$-alkyl.

9. The method of claim 8, wherein (ii) is applied in an amount of from 20 to 99.9% by weight, based on the total weight of the formulation.

10. The method of claim 8, wherein (i) comprises, in each case based on the total weight of the formulation from 0 to 70% by weight of water; and from 0.1 tot 60% by weight of at least one adjuvant and/or additive.

11. The method of claim 10, wherein (i) further comprises from 2 to 70% by weight, based on the total weight of the formulation, of at least tone active ingredient for plant treatment.

* * * * *